United States Patent [19]

Gerster

[11] Patent Number: 4,472,406

[45] Date of Patent: Sep. 18, 1984

[54] ANTIMICROBIAL 6,7-DIHYDRO-8-(IMIDAZOL-1-YL)-5-METHYL-1-OXO-1H,5H-BENZO[IJ]QUINOLIZINE-2-CARBOXYLIC ACIDS AND DERIVATIVES

[75] Inventor: John F. Gerster, Woodbury, Minn.

[73] Assignee: Riker Laboratories, Inc., St. Paul, Minn.

[21] Appl. No.: 441,246

[22] Filed: Nov. 12, 1982

[51] Int. Cl.$^3$ .................. A01N 43/50; A61K 31/47; C07D 455/04
[52] U.S. Cl. ...................... 424/258; 546/5; 546/94; 546/165; 546/167; 546/171
[58] Field of Search ............ 546/94, 5; 424/258; 544/101

[56] References Cited

U.S. PATENT DOCUMENTS 3,896,131 7/1975 Gerster .............. 424/258 X
4,404,207 9/1983 Stern .................... 546/94

FOREIGN PATENT DOCUMENTS 5788182 6/1982 Japan .
2086905 5/1982 United Kingdom .......... 546/94

OTHER PUBLICATIONS

Abstract of Japanese Patent Application 106,776 (published Dec. 16, 1980).
Abstract for Japanese Laid-Open Application No. 57-88183 (published Nov. 21, 1980).

*Primary Examiner*—Richard A. Schwartz
*Attorney, Agent, or Firm*—Donald M. Sell; James A. Smith; Robert W. Sprague

[57] ABSTRACT

Certain 6,7-dihydro-8-(imidazol-1-yl)-1-oxo-1H,5H-benzo[ij]quinolizine-2-carboxylic acids are disclosed as potent antimicrobial agents with an unusual spectrum of activity. Esters, acyl chlorides, alkylaminoalkyl ester salts, salts of a nitrogen atom of the imidazole ring, and pharmaceutically acceptable carboxylate salts are also disclosed. Novel synthetic intermediates are also described.

5 Claims, No Drawings

ANTIMICROBIAL 6,7-DIHYDRO-8-(IMIDAZOL-1-YL)-5-METHYL-1-OXO-1H,5H-BENZO[IJ]QUINOLIZINE-2-CARBOXYLIC ACIDS AND DERIVATIVES

TECHNICAL FIELD

This invention relates to heterocyclic compounds useful as antimicrobials. More particularly, it relates to 8-substituted 6,7-dihydro-5-methyl-1-oxo-1H,5H-benzo[ij]-quinolizine-2-carboxylic acids and derivatives thereof. The pharmacological use of the compounds of the invention as antimicrobial agents, pharmaceutical compositions containing the compounds and intermediates for preparing these compounds are also included within the scope of the invention.

BACKGROUND OF THE INVENTION

U.S. Pat. No. 3,896,131 describes a broad class of 6,7-dihydro-5-methyl-1-oxo-1H,5H-benzo[ij]quinolizine-2-carboxylic acids as antimicrobial agents. The patent specifically discloses many compounds substituted by common substituents on the benzo ring. It has now been found that compounds substituted at the 8 position of the benzo ring by an imidazole ring exhibit enhanced antimicrobial activity.

Japanese patent application No. 106776 which was published August 22, 1979, discloses benzo[ij]quinolizines having a heterocyclic piperazino group substituent on the benzo[ij]quinolizine ring. Compounds in which one of nitrogen atoms of the piperazino group is substituted are also disclosed.

DESCRIPTION OF THE INVENTION

The present invention relates to novel 6,7-dihydro-8-(imidazol-1-yl)-5-methyl-1-oxo-1H,5H-benzo[ij]-quinolizine-2-carboxylic acids and their derivatives. This invention also relates to the pharmacological use of these compounds as antimicrobial agents and to pharmaceutical compositions comprising these compounds. This invention also relates to intermediates for preparing these compounds.

Specifically, this invention relates to the novel 6,7-dihydro-8-(imidazol-1-yl)-5-methyl-1-oxo-1H,5H-benzo[ij]-quinolizine-2-carboxylic acids of Formula I

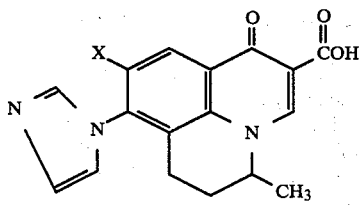

Formula I wherein X is hydrogen or halogen selected from bromine, chlorine and fluorine, or an ester, acyl chloride, alkylaminoalkyl ester salt, salt involving a nitrogen atom of the imidazole ring, or pharmaceutically acceptable carboxylate salt thereof. These compounds and their formulations are useful antimicrobials. The substituent X is preferably hydrogen or fluorine, fluorine being most preferred.

The present invention also relates to novel intermediates of Formula II

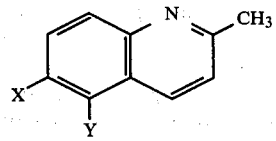

Formula II wherein X is hydrogen or halogen; and Y is imidazol-1-yl, 2-mercaptoimidazol-1-yl, -N=C=S or

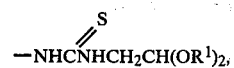

wherein each $R^1$ is independently an alkyl group containing 1 to about 4 carbons.

The present invention further relates to novel intermediates of Formula III

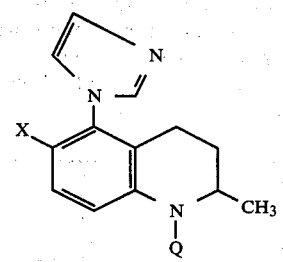

Formula III wherein X is hydrogen or halogen; and Q is hydrogen or $-CH=C(CO_2CH_2CH_3)_2$.

Compounds of Formula I have an optically active carbon at the 5-position. All such optical isomers are included within the scope of the invention.

It is well known to the art that pharmaceutically acceptable salts such as alkali metal, alkaline earth, aluminum, iron, silver and other metal and amine salts of pharmaceutically-active acids are the equivalents of the acids in terms of activity, and in some cases may even offer advantages in absorption, formulation and the like. Pharmaceutically-acceptable carboxylate salts of the free acid compounds of Formula I are readily prepared by reaction of the acid with a base and subsequent evaporation to dryness. The base may be organic, e.g., sodium methoxide or an amine, or inorganic, e.g., sodium hydroxide. Alternatively, the cation of a carboxylate salt, e.g., sodium, may be displaced by a second cation such as calcium or magnesium when the salt of the second cation is more insoluble in a selected solvent.

Other useful derivatives of the compounds of Formula I include the acyl chlorides, esters and alkylaminoalkyl ester salts thereof. In the acyl chloride derivatives, the hydroxyl portion of the carboxylic acid group is removed and replaced with chlorine. In the ester derivatives, the hydrogen portion of the carboxylic acid group is replaced with an alkyl or substituted-alkyl, preferably an alkylaminoalkyl group.

Esters and acyl chlorides of the compounds of Formula I may be obtained as intermediates during the preparation of the acidic compound. In some cases, the esters may be prepared directly using standard synthetic methods. These esters and acyl chlorides exhibit antimicrobial activity, but they are primarily of interest as synthetic intermediates, although in some instances hydrolyzable or salt-forming esters may be of interest as therapeutic agents. Preferred esters are alkyl esters and alkylaminoalkyl esters having one to four carbon atoms in the alkyl group. Especially preferred are salts of alkylaminoalkyl esters such as hydrochloride salts of dimethylaminoethyl esters.

Ester derivatives are readily prepared by reacting the free acid of Formula I with thionyl chloride to provide the novel acyl chloride derivatives. The acyl chloride is reacted with the appropriate alcohol to provide the desired ester.

Still other useful derivatives of the compounds of Formula I are salts involving a nitrogen atom of the imidazole ring. Such derivatives are obtained by reacting the compound of Formula I with, for example, a suitable mineral acid. Especially preferred are the hydrochloride salts obtained by reacting the compound of Formula I with hydrochloric acid.

The antimicrobial activity of the compounds of Formula I and their derivatives can be demonstrated by the known, standard plate dilution method for bacterial susceptibility testing of fastidious microorganisms towards antibiotics, sulfonamides and other chemotherapeutic agents. Tryptone soy agar (oxoid) of the following composition is the culture medium.

| Oxoid tryptone | 15 g. |
| Oxoid soy peptone | 2 g. |
| Sodium chloride | 5 g. |
| Oxoid agar-agar No. 3 | 15 g. |
| Water | 1 liter |

Using this test, compounds of Formula I and their derivatives have been found to have a broad spectrum of activity against gram-positive and gram-negative microorganisms.

The compounds of Formula I and their derivatives are active against microorganisms either in the absence or presence of 10 percent horse serum.

The test procedure used to determine activity as employed in connection with the present invention provides information on the amount of a compound which gives complete inhibition, partial inhibition or no inhibition of microbial growth on the agar plates. In the tests, the selected compound is added to the agar medium to give concentrations of zero, one, ten and one hundred milligrams per liter. A series of plates with these concentrations is prepared. Ten percent horse serum is added to one series of such plates. Aliquots of broth culture of any of twelve species of microorganisms are inoculated onto the agar plates containing the various compound concentrations. The plates are incubated at 37° C. in a 10 percent carbon dioxide atmosphere for 18-24 hours. The microbial growth on each plate is read visually, and minimum inhibitory concentrations (for partial or complete inhibition) are recorded. Some of the microorganisms which are used for this test are:

1. *Staphylococcus aureus*
2. *Bacillus subtilis*
3. *Escherichia coli*
4. *Pseudomonas aeruginosa*
5. *Streptococcus sp.* *
6. *Aspergillus niger*
7. *Candida albicans*
8. *Acinetobacter lwoffi*
9. *Acinetobacter anitratum*
10. *Klebsiella pneumoniae*
11. *Streptococcus fecaelis*
12. *Serratia marcescens*

*Strains isolated from dental caries in rats or hamsters at the National Institute of Dental Health and grown in PFY or APT agar.

The compounds of Formula I and their derivatives possess antimicrobial activity towards one or more of the above microorganisms. Of specific significance is the high level of activity of the 9-fluoro-substituted compound of Formula I and its salts against *Pseudomonas aeruginosa*, a particularly bothersome species associated with many topical infections. This type of activity is unusual in benzoquinolizine-type antibacterials.

It will be understood by those skilled in the art that the species used are representative indicator species, as it would be impractical to screen against all bacteria. It is well known in the art that broad spectrum activity can be predicted on the basis of activity shown against selected representative bacterial species.

The compounds of Formula I and their derivatives are active when administered orally to animals. They are excreted in the urine, and are effective urinary tract antibacterials in mammals. They may also be used in the treatment of pulmonary infections, soft tissue infections, burn infections and bacteremias.

Compounds of Formula I and their derivatives are active against microorganisms in vitro or topically. In vitro activity is useful in itself, since antimicrobial agents may be used for disinfecting and sterilizing, e.g., medical and dental equipment, as components of disinfecting solutions.

The acute oral toxicity of the compounds of Formula I and their derivatives generally is moderate to low compared with the effective oral dose, and they have an acceptable therapeutic ratio ($LD_{50}/ED_{50}$) of greater than 80.

The compounds of Formula I are generally white crystalline materials when purified. They are substantially insoluble in water, lower alcohols or hydrocarbons and are more soluble in halogenated solvents, N,N-dimethylformamide and the like. The salts, especially the alkali metal and hydrochloride salts, have appreciable solubility in water and lower alcohols.

The compounds of Formula I and their derivatives may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing objects to be treated therein, or by local application to an infected area.

The amount of a compound used to treat, for example, a microbial urinary infection by oral administration will be an effective amount less than a toxic amount. The amount to be administered to control an infection will depend on the species, sex, weight, physical condition and many other factors, but this judgment is well within the skill of the medical art. Usually the amount will be less than 100 mg/kg per dose. Conveniently this is administered in the form of the usual pharmaceutical preparations such as capsules, tablets, emulsions, solutions and the like. Excipients, fillers, coatings, etc. are employed with tablets or capsules, as is well known in the art.

It is known to the art that antimicrobial agents are used as growth promoters in various animal and bird species. Although not yet verified, it is inferred from their outstanding antimicrobial activity that the compounds of Formula I and their derivatives can be used for this purpose also. These compounds may also be used for the control of microbial (e.g., *Erwinia amylovora*) infections of plants, e.g., by spraying or dusting a formulation of these compounds on the affected area.
The compounds of Formula I may be prepared as described in the following Reaction Scheme:
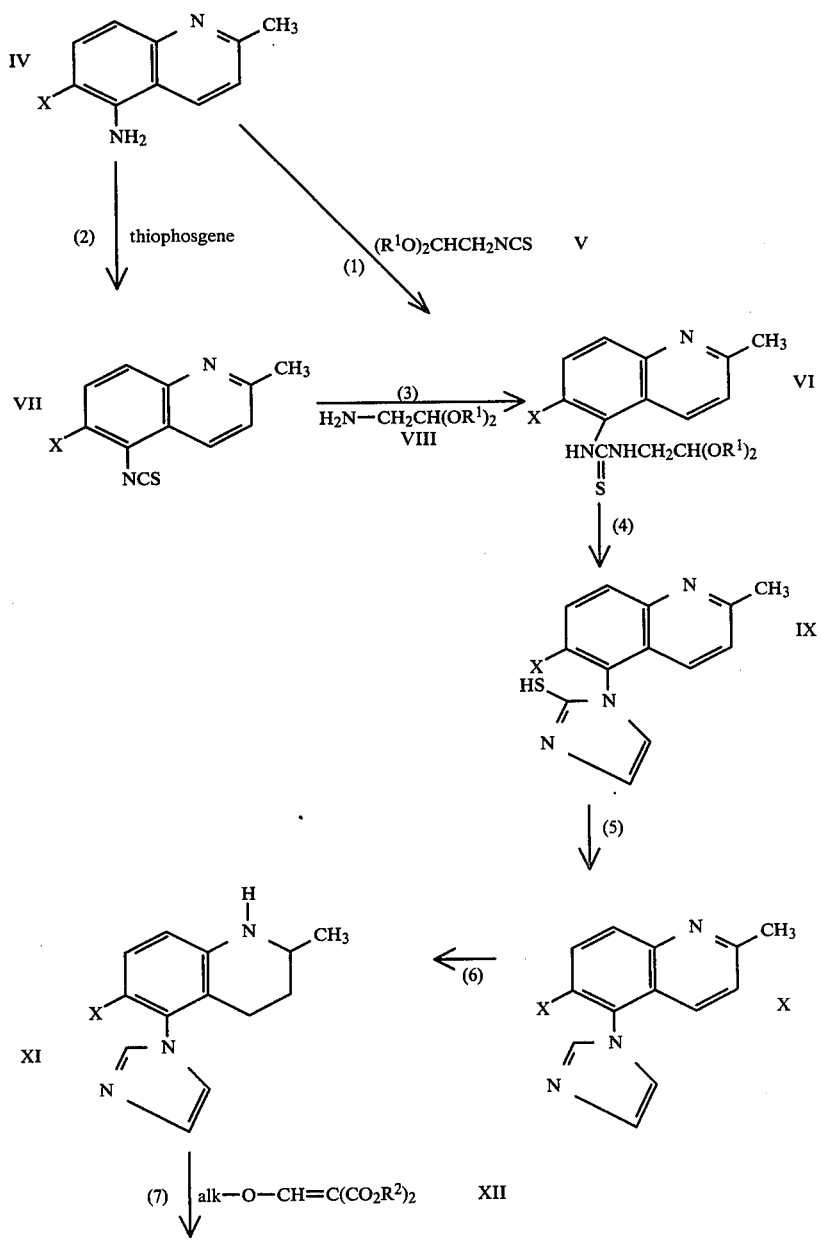

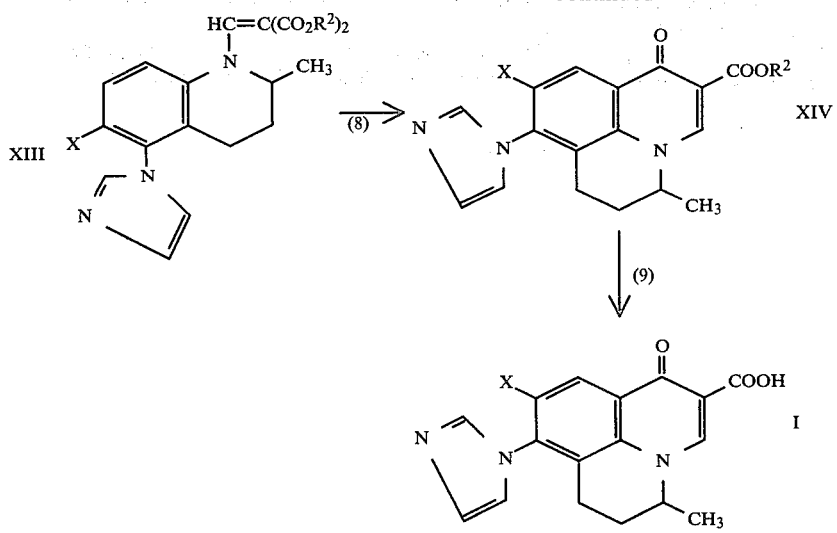

wherein X is as previously defined herein; and alk and R[1] and R[2] are independently alkyl groups containing 1 to about 4 carbon atoms, and preferably 1 to 2 carbon atoms.

In the first step of the above-illustrated reaction scheme, the known compound 5-amino-2-methylquinoline (optionally substituted in the 6-position by halogen) of Formula IV is condensed with a 2,2-dialkoxyethyl isothiocyanate of Formula V to provide the novel N-(2,2-dialkoxyethyl)-N'-(2-methylquinolin-5-yl)thiourea of Formula VI. The condensation reaction is carried out by heating the reactants at a temperature of between about 50° and 100° C. in the absence of solvent. Preferred 2,2-dialkoxyethyl isothiocyanates of Formula V are 2,2-dimethoxyethyl isothiocyanate and 2,2-diethoxyethyl isothiocyanate.

Alternatively, the N-(2,2-dialkoxyethyl)-N'-(2-methylquinolin-5-yl)thiourea of Formula VI may be prepared following steps (2) and (3) of the reaction scheme. In step (2), the known 5-amino-2-methylquinoline (optionally substituted in the 6-position by halogen) of Formula IV is reacted with thiophosgene in diethyl ether and in the presence of aqueous sodium bicarbonate to provide the novel intermediate 5-isothiocyanato-2-methylquinoline of Formula VII. Subsequently, the intermediate of Formula VII is reacted at 50° to 100° C. with an aminoacetaldehyde dialkyl acetal of Formula VIII in step (3) to provide the N-(2,2-dialkoxyethyl)-N'-(2-methylquinolin-5-yl)thiourea of Formula VI. The preferred dialkyl acetals of Formula VIII are the dimethyl and diethyl acetals.

In step (4), the dialkoxyethylthiourea group of the intermediate of Formula VI is cyclized by heating at a temperature of 50° to 100° C. in the presence of a strong inorganic acid such as hydrochloric acid to provide the novel 5-(2-mercaptoimidazol-1-yl)-2-methylquinoline of Formula IX.

Step (5) involves desulfurization of the intermediate of Formula IX to provide the novel intermediate 5-(imidazol-1-yl)-2-methylquinoline of Formula X. Step (5) is carried out by heating the intermediate of Formula IX with nitric acid, or preferably, by reducing that intermediate with Raney nickel in ethanol.

In step (6) the intermediate of Formula X is reduced to provide the novel intermediate 5-(imidazol-1-yl)-1,2,3,4-tetrahydro-2-methylquinoline of Formula XI.

This reduction may be accomplished using pyridine-diborane complex in a concentrated alkanoic acid. Preferably this reduction is accomplished using platinum on carbon in acetic acid.

The 5-(imidazol-1-yl)-1,2,3,4-tetrahydro-2-methylquinoline of Formula XI is condensed with a dialkyl alkoxymethylenemalonate of Formula XII in step (7). The preferred dialkyl alkoxymethylenemalonate is diethyl ethoxymethylenemalonate since it is most readily available. The condensation reaction requires heating of the reactants until the reaction is complete as determined by chromatographic analysis. The reaction is conducted in the absence of solvent at a temperature of 100° to 200° C. for several hours. It is preferred that the reaction be conducted at a temperature of 140°-150° C. for two hours. Alternatively, the reaction may be conducted in the presence of an inert organic solvent which forms an azeotropic mixture with the alcohol formed upon condensation of the dialkyl alkoxymethylenemalonate (e.g., ethanol where diethyl ethoxymethylenemalonate is employed). The reaction mixture is heated at its reflux temperature and the azeotropic mixture comprising the alcohol and the organic solvent is collected, for example, in a Dean Stark trap. Fresh organic solvent is generally added to the reaction mixture as the solvent is depleted during distillation. Removal of the alcohol from the reaction mixture drives the condensation reaction to substantial completion and increases the yield. The product of step (7) is the novel intermediate of Formula XIII. This intermediate may be isolated as an oil or the product of step (7) may be used directly in step (8) below without isolation of the intermediate.

In step (8) the intermediate of Formula XIII is cyclized to form the ester of Formula XIV. The cyclization step is carried out by heating the intermediate of Formula XIII in the presence of polyphosphoric acid. The temperature of the reaction is preferably between about 150° and 160° C.

The ester of Formula XIV is hydrolyzed in step (9) by conventional means to provide a 6,7-dihydro-8-(imidazol-1-yl)-5-methyl-1-oxo-1H,5H-benzo[ij]quinolizine-2-carboxylic acid of Formula I.

The following examples are provided to illustrate the synthetic methods useful to obtain compounds of the invention, and are not intended to be limiting of the invention.

EXAMPLE 1

Synthesis of 6,7-Dihydro-9-fluoro-8-(imidazol-1-yl)5-methyl-1-oxo-1H,5H-benzo[ij]quinolizine-2-carboxylic Acid

Part A

To 17.85 g (0.1013 mole) of 5-amino-6-fluoro-2-methylquinoline was added 19.5 g (0.1114 mole) of 2,2-diethoxyethylisothiocyanate and the mixture was heated at 80°–90° C. for 1.5 hours. The residue was slurried in ethanol, separated by filtration, washed with ethanol and then recrystallized from ethanol to provide N-(2,2-diethoxyethyl)-N'-(6-fluoro-2-methylquinolin-5-yl)thiourea, m.p. 189°–191° C.

Analysis: Calculated for $C_{17}H_{22}FN_3O_2S$: %C, 58.1; %H, 6.3; %N, 12.1; Found: %C, 58.3; %H, 6.5; %N, 11.9.

Part B

A mixture of 26.2 g (0.0746 mole) of N-(2,2-diethoxyethyl)-N'-(6-fluoro-2-methylquinoline-5-yl)thiourea and 250 ml of 10% hydrochloric acid was heated on a steam bath for two hours, then allowed to cool to about 20° C. The solution was poured into saturated sodium bicarbonate solution. After the foaming subsided, the solid was separated by filtration, washed with water and dried. Recrystallization from ethanol provided white solid 6-fluoro-5-(2-mercaptoimidazol-1-yl)-2-methylquinoline, m.p.>250° C.

Analysis: Calculated for $C_{13}H_{10}FN_3S$: %C, 60.2; %H, 3.9; %N, 16.2; Found: %C, 59.9; %H, 3.9; %N, 16.6.

Part C

To a flask containing 16.2 g (0.0625 mole) of 6-fluoro-5-(2-mercaptoimidazol-1-yl)-2-methylquinoline was added with stirring 300 ml of 20% nitric acid. After stirring for 30 minutes, the mixture was heated on a steam bath for an additional 30 minutes. The solution was allowed to cool to about 20° C., then made basic (pH 8 to 10) by adding 50% aqueous sodium hydroxide while cooling with an ice bath. The solid precipitate was separated by filtration, washed with water and dried. Recrystallization from aqueous ethanol provided 6-fluoro-5-(imidazol-1-yl)-2-methylquinoline, m.p. 159°–161° C.

Analysis: Calculated for $C_{13}H_{10}FN_3$: %C, 68.7; %H, 4.4; %N, 18.5; Found: %C, 68.6; %H, 4.4; %N, 18.2.

Part D

A solution of 10.2 g (44.9 mmole) of 6-fluoro-5-(imidazol-1-yl)-2-methylquinoline, 16.7 g (180 mmole) of pyridine:diborane complex (that commercially available from Aldrich) and 200 ml of glacial acetic was stirred for about 22 hours at about 20° C. The solution was evaporated to reduce its volume, then 100 ml of 10% hydrochloric acid was added in small portions. The solution was heated on a steam bath for about one hour, then cooled with an ice bath and basified (pH 9 to 10) with 10% aqueous sodium hydroxide. The solid was separated by filtration, washed with water, and dissolved in ethyl acetate and dried. Recrystallization from aqueous ethanol provided 6-fluoro-5-(imidazol-1-yl)-1,2,3,4-tetrahydro-2-methylquinoline, m.p. 162°–164° C.

Analysis: Calculated for $C_{13}H_{14}FN_3$: %C, 67.5; %H, 6.1; %N, 18.2; Found: %C, 67.5; %H, 6.1; %N, 18.0.

Part E

A mixture of 8.7 g (37.6 mmole) of 6-fluoro-5-(imidazol-1-yl)-1,2,3,4-tetrahydro-2-methylquinoline and 8.94 g (41.4 mmole) of diethyl ethoxymethylenemalonate was heated at 150°–160° C. for 1.5 hours and was then allowed to cool to about 20° C. A small sample of the reaction mixture was checked by thin layer chromatography in ethyl acetate and infrared spectroscopy to determine the presence of the desired intermediate, diethyl 2-[N-(6-fluoro-5-(imidazol-1-yl)-1,2,3,4-tetrahydro-2-methylquinolinyl)]methylenemalonate. The presence of the desired product was confirmed.

Polyphosphoric acid (70 g) was added to the reaction mixture, and the mixture was heated on a steam bath until foaming began. Heating was continued for about 0.75 hour and was accompanied by manual stirring. Water (about 200 ml) was added gradually, and the pH of the mixture was then adjusted to 6 by the addition of 50% aqueous sodium hydroxide (with cooling). The product, which separated as an oil and gradually solidified, was 16.5 g of crude ethyl 6,7-dihydro-9-fluoro-8-(imidazol-1-yl)-5-methyl-1-oxo-1H,5H-benzo[ij]quinoline-2-carboxylate.

The ester was mixed with 100 ml of 10% hydrochloric acid, and the mixture was heated at its reflux temperature for one hour. The mixture was allowed to cool to about 20° C., and concentrated ammonium hydroxide was added until the pH of the mixture was about 7. The solid formed was separated by filtration, washed with water and dried. The solid was slurried in hot N,N-dimethylformamide and filtered from the mixture to provide 6,7-dihydro-9-fluoro-8-(imidazol-1-yl)-5-methyl-1-oxo-1H,5H-benzo[ij]-quinolizine-2-carboxylic acid, m.p.>250° C.

Analysis: Calculated for $C_{17}H_{14}FN_3O_3$: %C, 62.4; %H, 4.3; %N, 12.8; Found: %C, 62.3; %H, 4.3; %N, 12.5.

EXAMPLE 2

Synthesis of 6,7-Dihydro-8-(imidazol-1-yl)-5-methyl-1-oxo-1H,5H-benzo[ij]quinolizine-2-carboxylic Acid

Part A

Using the method of Example 1, Part A, 5-amino-2-methylquinoline was reacted in dichloromethane to provide N-(2,2-diethoxyethyl)-N'-(2-methylquinolin-5-yl)thiourea, m.p. 181°–185° C. after recrystallization from ethanol. Analysis:

Calculated for $C_{15}H_{19}N_3O_2S$: %C, 59.0; %H, 6.3; %N, 13.8; Found: %C, 59.0; %H, 6.4; %N, 13.8.

Part B

A mixture of 8.6 g (28 mmole) of N-(2,2-diethoxyethyl)-N'-(2-methylquinolin-5-yl)thiourea and 100 ml of 10% hydrochloric acid was heated on a steam bath for one hour. The solution was allowed to cool to about 20° C., and was then poured with vigorous stirring into a mixture of ice and ammonium hydroxide. The solid was separated by filtration, washed with water, and triturated with ethyl acetate to provide solid 5-(2-mercaptoimidazol-1-yl)-2-methylquinoline.

Part C

A solution of 4.8 g (0.020 mole) of 5-(2-mercaptoimidazol-1-yl)-2-methylquinoline in 20 ml of 10% nitric acid was heated to 70°–80° C. on a steam bath, and 90% nitric acid was added dropwise with stirring until a vigorous evolution of nitrous oxide was observed. The solution was allowed to cool to about 20° C., ice was added and the solution was basified with 25% aqueous sodium hydroxide. The mixture was extracted with ethyl acetate, and the extracts were dried over sodium chloride and charcoal and then evaporated. The residue was recrystallized twice from an acetone-hexane mixture to provide 5-(imidazoly-1-yl)-2-methylquinoline, m.p. 155.5°–157.5° C.

Analysis: Calculated for $C_{13}H_{11}N_3$: %C, 74.6; %H, 5.3; %N, 20.1; Found: %C 74.8; %H, 5.1; %N, 20.3.

Part D

Using the method of Example 1, Part D, 5-(imidazol-1-yl)-2-methylquinoline is converted to 5-(imidazol-1-yl)-1,2,3,4-tetrahydro-2-methylquinoline.

Part E

Using the procedure of Example 1, Part E, 5-(imidazol-1-yl)-1,2,3,4-tetrahydro-2-methylquinoline is reacted with diethyl ethoxymethylenemalonate to provide diethyl 2-[N-(5-(imidazol-1-yl)-1,2,3,4-tetrahydro-2-methylquinolinyl)]-methylenemalonate. This intermediate is further reacted in polyphosphoric acid to provide ethyl 6,7-dihydro-8-(imidazol-1-yl)-5-methyl-1-oxo-1H,5H-benzo[ij]-quinolizine-2-carboxylate. This ester intermediate is hydrolyzed to 6,7-dihydro-8-(imidazol-1-yl)-5-methyl-1-oxo-1H,5H-benzo[ij]quinolizine-2-carboxylic acid.

EXAMPLE 3

To a mixture of 0.500 g (1.53 mmole) of 6,7-dihydro-9-fluoro-8-(imidazol-1-yl)-5-methyl-1-oxo-1H,5H-benzo[ij]quinolizine-2-carboxylic acid (from Example 1) and 10 ml of water was added 15.3 ml of 0.1 N aqueous sodium hydroxide (1.53 mmole). The mixture was filtered, an equal volume of ethanol added, and the solution evaporated to dryness to give tan crystals of sodium 6,7-dihydro-9-fluoro-8-(imidazol-1-yl)-5-methyl-1-oxo-1H,5H-benzo[ij]quinolizine-2-carboxylate hydrate, m.p. >250° C.

Analysis: Calculated for $C_{17}H_{13}FNaN_3O_3 \cdot 1.25\ H_2O$: %C, 54.9; %H, 4.2; %N, 11.3; Found: %C, 54.9; %H, 4.4; %N, 10.7.

EXAMPLE 4

To a mixture of 0.500 g (15.3 mmole) of 6,7-dihydro-9-fluoro-8-(imidazol-1-yl)-5-methyl-1-oxo1H,5H-benzo[ij]quinolizine-2-carboxylic acid (from Example 1) and 10 ml of water was added dropwise concentrated hydrochloric acid until the pH of the mixture was between 2 and 3 as indicated by litmus paper. The mixture was stirred and heated on a steam bath for about 20 minutes. An equal volume of ethanol was added, and the resulting white solid was separated by filtration, washed with ethanol and dried. The product was 6,7-dihydro-9-fluoro-8-(imidazol-1-yl)-5-methyl-1-oxo1H,5H-benzo[ij]quinolizine-2-carboxylic acid hydrochloride, m.p. >250° C.

Analysis: Calculated for $C_{17}H_{15}ClFN_3O_3$: %C, 56.1; %H, 4.2; %N, 11.55; Found: %C, 56.0; %H, 4.2; %N, 11.5.

EXAMPLE 5

A mixture of 30 g (0.115 mmole) of 6-fluoro-2-methyl-5-(2-mercaptoimidazol-1-yl)quinoline, 60 ml of ammonium hydroxide and 300 ml of 60% aqueous ethanol was heated to 50°–55° C. and 201 g of Raney nickel was added. The mixture was heated to reflux and maintained at reflux for four hours, at which time it was filtered. The residue was washed with hot aqueous ethanol, and the washings and filtrate were combined and evaporated to provide 6-fluoro-5-(imidazol-1-yl)-2-methylquinoline as a yellow solid.

EXAMPLE 6

To a solution of 4.2 g (18 mmole) of 6-fluoro-5-(imidazol-1-yl)-2-methylquinoline in 75 ml of acetic acid was added 0.5 g of platinum on carbon, and the mixture was reduced on a Paar apparatus. After one day the mixture was filtered, the filtrate was evaporated and the residue was diluted with water. The aqueous mixture was basified with 10% aqueous sodium hydroxide solution. The off-white solid was separated by filtration to provide 6-fluoro-5-(imidazol-1-yl)-2-methyl-1,2,3,4-tetrahydroquinoline.

What is claimed is:

1. A compound of the formula

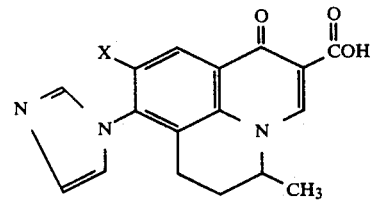

wherein X is hydrogen or halogen selected from fluorine, chlorine or bromine; or a derivative selected from the group consisting of an alkyl ester containing 1 to 4 carbon atoms in the alkyl group, the acyl chloride, an alkylaminoalkyl ester containing 1 to 4 carbon atoms in the alkyl groups, an alkylaminoalkyl ester salt containing 1 to 4 carbon atoms in the alkyl groups, a salt involving a nitrogen atom of the imidazole ring, and a pharmaceutically acceptable carboxylate salt thereof.

2. A compound according to claim 1 which is a carboxylate salt selected from an alkali metal and alkaline earth carboxylate salts.

3. The compound 6,7-dihydro-8-(imidazol-1-yl)-9-fluoro-5-methyl-1-oxo-1H,5H-benzo[ij]quinolizine-2-carboxylic acid or a salt thereof according to claim 1.

4. An antimicrobial composition comprising an effective amount of a compound according to claim 1 and a pharmaceutically acceptable carrier.

5. A method of inhibiting the growth of bacteria, comprising contacting said bacteria with an effective amount of a compound according to claim 1.